United States Patent [19]

Uesugi et al.

[11] Patent Number: 5,304,381
[45] Date of Patent: Apr. 19, 1994

[54] STABILIZATION OF POLYPRENYL COMPOUND

[75] Inventors: Keizo Uesugi; Nobutaka Noda, both of Aichi; Michiru Tanaka, Tokyo; Masanori Kayano, Saitama, all of Japan

[73] Assignee: Eisai Co., Ltd., Tokyo, Japan

[21] Appl. No.: 487,665

[22] Filed: Mar. 2, 1990

[30] Foreign Application Priority Data

Mar. 17, 1989 [JP] Japan .................................. 1-65384
Mar. 17, 1989 [JP] Japan .................................. 1-65385

[51] Int. Cl.$^5$ ..................... A61K 47/22; A61K 47/12; A61K 47/22; A61K 9/48
[52] U.S. Cl. ..................... 424/484; 424/456; 424/451; 514/962; 514/970
[58] Field of Search ................ 424/456, 484; 514/962, 514/970, 420; 548/500, 501

[56] References Cited

U.S. PATENT DOCUMENTS

| | | | |
|---|---|---|---|
| 3,252,865 | 5/1966 | Kläui | 514/970 |
| 3,943,238 | 3/1976 | Kobayashi et al. | 514/962 |
| 4,455,316 | 6/1984 | Yamatsu et al. | 514/419 |
| 4,496,536 | 1/1985 | Möller et al. | 514/458 |
| 4,711,894 | 12/1987 | Wenzel et al. | 514/970 |

FOREIGN PATENT DOCUMENTS

| | | |
|---|---|---|
| 0138216A3 | 4/1985 | European Pat. Off. . |
| 0407815A2 | 1/1991 | European Pat. Off. . |
| 58-32873 | 2/1983 | Japan . |

OTHER PUBLICATIONS

S. Budavari et al, ed., The Merck Index, 11th ed, Merck & Co, Rahway N.J., 1989, p. 1495.

Primary Examiner—Edward Webman
Attorney, Agent, or Firm—Flynn, Thiel, Boutell & Tanis

[57] ABSTRACT

A polyprenyl compound having formula (1) is stabilized by a tocopherol, an organic acid, a neutral amino acid or a basic amino acid:

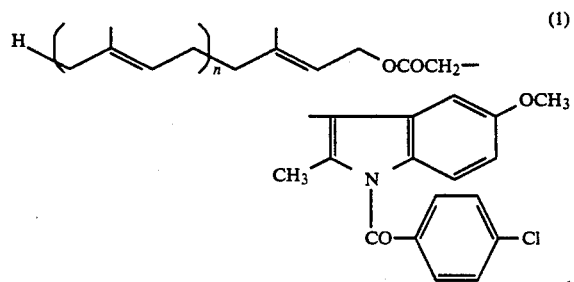

in which n is an integer of 1 to 3.

11 Claims, 1 Drawing Sheet

STABILIZATION OF POLYPRENYL COMPOUND

The present invention relates to a process for producing a stable polyprenyl compound-containing composition. In particular, the present invention relates to a process for producing a stable polyprenyl compound-containing composition by adding a tocopherol, an organic acid, or a neutral or basic amino acid thereto.

Prior Art

Polyprenyl compounds of the general formula (1):

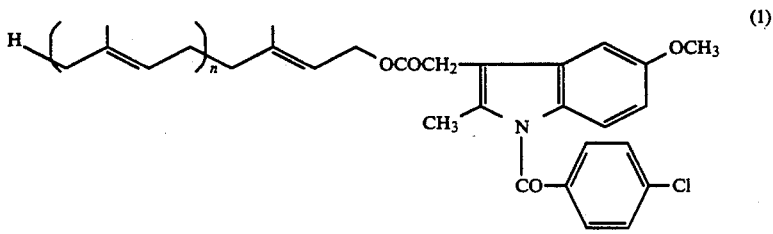

(1)

wherein n represents an integer of 1 to 3, where developed as prodrugs for indomethacin and have a low toxicity and a remarkable antiinflammatory effect.

Various antiinflammatory agents such as steroid hormones, nonsteroid drugs and antiphlogistic enzyme preparations were developed and, recently, intensive investigations have been made for the purpose of developing nonsteroid antiinflammatory agents. They particularly include acidic compounds such as indoleacetic acids, e.g., indomethacin, phenylacetic acid compounds, e.g., ibuprofen, and salicyclic acid compounds, e.g., aspirin and salicylic acid.

However, various clinical adverse reactions, such as gastrointestinal and renal troubles, caused by the nonsteroid compounds have been reported.

Indomethacin, which is a typical indoleacetic acid compound having a strong potency, among the nonsteroid antiinflammatory agents is frequency used clinically in the treatment of rheumatism and its therapeutical effect has been recognized. However, repeated administration of the medicine for a long period of time is necessary for the treatment of rheumatism or the like and cause serious side effects of the stomach, central nervous system, kidney, etc., thereby hindering the practical application thereof.

In particular, since most of the prenyl compounds are fat-soluble, they can be adsorbed onto a powder having a large surface area, suitably for the preparation of a solid product for oral administration. They are accordingly easy to oxidize and decrease in quality.

It is reported that indomethacin, which is a typical indoleacetic acid compound, while relatively stable in a neutral environment, its N-amide bond was likely to decompose in a basic environment [see Shigeru Goto et al., 'Yakuzaigaku (Pharmacology)', 33 (3), 139 (1973) and A. Cipicinani et al., J. Pharm. Sciences, 72 (9), 1975 (1983)].

3,7,11,15-Tetramethyl-2,6,10,14-hexadecatetraenyl 1-(p-chlorobenzoyl)-2-methyl-5-methoxy-3-indolylacetate (hereinafter referred to as indomethacin farnesyl) of the above general formula (1), which is a prodrug for indomethacin, was developed as an antiinflammatory agent having a prolonged action and only a weak adverse reaction (see Japanese Patent Laid-Open No. 15940/1983).

The polyprenyl compounds represented by the above general formula (1) are fat-soluble drugs. In producing a preparation of a fat-soluble medicine for oral administration, it is directly filled in a soft capsule or, alternatively, it is adsorbed onto a powder having a large surface area and then filled in a hard capsule.

It is known that the shell of the soft capsule is insufficiently soluble and deteriorates with time. In addition, it has defects in dispensing. There has been disclosed a shell of the soft capsule type prepared by adding tartaric acid, glycerol, etc. to gelatin as the main component to obtain stabilization of the capsule (see Japanese Patent Publication No. 48909/1982). Further, an acylated gelatin shell prepared by acylating an amino group of the gelatin molecule with an organic acid has also been disclosed (see Japanese Patent Publication No. 103316/1983). However, many soft capsules have problems with their solubility and maintenance of their qualities.

Under these circumstances, the inventors have made pharmaceutical investigations for the production of a preparation of a polyprenyl compound of the above general formula (1) with a hard capsule. However, in the production of a solid preparation for oral administration containing a fat-soluble drug, such as a polyprenyl compound, disintegration of the hard capsule is a problem in the pharmaceutical design thereof.

Fat-soluble medicines such as polyprenyl compounds are combined with bile or a triglyceride to form a complex micelle, from which the medicine is released and adsorbed through microvilli of the small intestine into the blood or lymphatic vessels.

It was reported that there is an interrelationship between the dispersibility of a medicine and the adsorption thereof. The diameter of the particles of the medicinal agent must be reduced to form a dispersion. Emulsification process for dispersing a fat-soluble medicine, such as a polyprenyl compound in water, include a process wherein a surfactant capable of forming a micelle having a stable interfacial film, such as Polysorbate 80, is used and a process wherein the coalescence of the particles of the fat-soluble medicine is prevented by adsorbing the medicine on solid particles, such as silicon dioxide, or by adding a hydrophilic colloid, such as methylcellulose, to form an emulsion.

It is well known that a side chain having a double bond can easily be oxidized, and the inventors have found that s stable composition can be obtained by adding at least one compound selected from the group consisting of tocopherols and organic acids to the polyprenyl compound. The present invention has been completed on the basis of this finding.

After making pharmaceutical investigations, the inventors have found that the disintegratability of the hard capsule can be improved by adding a neutral or basic amino acid to a polyprenyl compound.

The inventors made investigations wherein a hydrophilic colloid, such as silicon dioxide, was used for improving the dispersibility of the polyprenyl compound.

The polyprenyl compound was inserted into a hard capsule and the disintegratability thereof was examined to reveal that, although the outer wall of the capsule was dissolved, the inner wall thereof remained in a jelly-like form to present the phenomenon of insufficient disintegration. It was found that gelatin in the capsule shell reacted with the polyprenyl compound to insolubilize the shell.

Supposely, the amine or carbonyl compound present in the gelatin molecule in the capsule shell reacted with impurities contained in the polyprenyl compound or with acid decomposition products.

Therefore, the amine or carbonyl compound in the gelatin molecules must be inactivated along with the impurities contained in the polyprenyl compound.

The inventors have found that the substances that cause the above defects can be inactivated by incorporating a neutral or basic amino acid into the polyprenyl compound. The present invention has been completed on the basis of this finding.

The invention provides a method for stabilizing a polyprenyl compound having the formula (1), comprising the step of mixing it with a stabilizing agent selected from the group consisting of a tocopherol, an organic acid, a neutral amino acid and a basic amino acid:

encapsulated in the shell, obtained by the method as defined above in which the stabilizing agent is selected from the group consisting of a neutral amino acid and a basic amino acid, (3) a pharmacological composition which comprises a therapeutically effective amount of the polyprenyl compound as defined above and an effective amount of the stabilizing agent as defined above and (4) a pharmacological composition which comprises a therapeutically effective amount of the polyprenyl compound as defined above, an effective amount of the stabilizing agent as defined above and a pharmacologically acceptable carrier.

The invention further provides a process for producing pharmacological hard capsules, which comprises the steps of mixing the polyprenyl compound as defined above with a stabilizing agent selected from the group consisting of a neutral amino acid and a basic amino acid and encapsulating the resulting mixture.

Thus, the present invention provides a process for producing a stable polyprenyl compound-containing composition characterized in that at least one compound selected from the group consisting of tocopherols and organic acids is added to a polyprenyl compound of the above general formula (1).

Among the compounds represented by the above general formula (1), a compound having a remarkable pharmacological effect is 3,7,11,15-tetramethyl-2,6,10,14-hexadecatetraenyl 1-(p-chlorobenzoyl)-2-methyl-5-methoxy-3-indolylacetate (hereinafter referred to as indomethacin farnesyl) represented by the following formula (2):

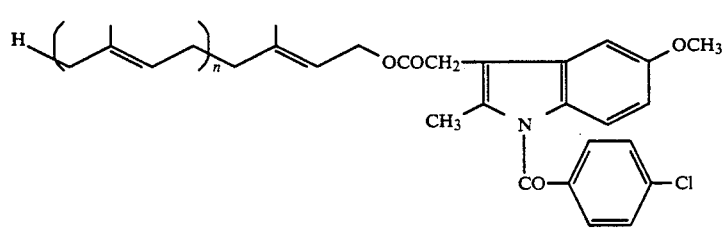

(1)

in which n is an integer of 1 to 3.

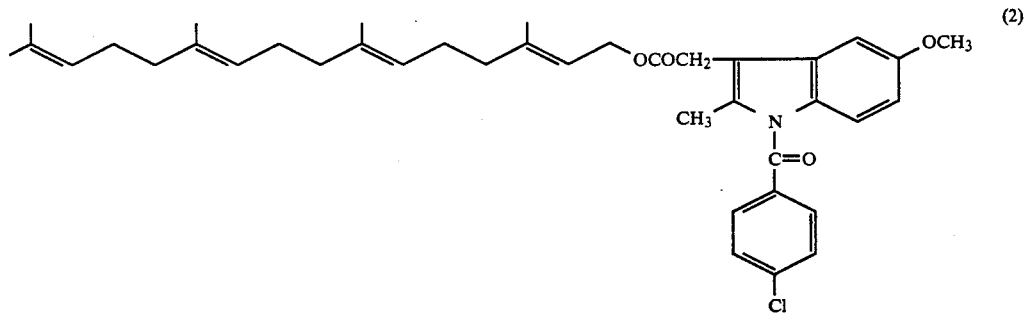

(2)

The most preferable polyprenyl compound is 3,7,11,15-tetramethyl-2,6,10,14-hexadecatetraenyl 1-(p-chlorobenzoly)-2-methyl-5-methoxy-3-indolylacetate or indomethacin farnesyl.

It is preferable that the tocopherol be selected from the group consisting of dl-α-tocopherol, d-δ-tocopherol and a natural tocopherol and the organic acid is selected from the group consisting of citric acid and tartaric acid.

The invention provides (1) a stabilized composition as obtained by the method as defined above, (2) hard capsules comprising a shell and the stabilized composition, The tocopherols used in order to obtain the stable composition is the present invention are free tocopherols or tocopherol derivatives which may be any of α-, β-, γ- and δ-homologs. An indispensible structure among them is the chroman nucleus of the tocopherols. The most desirable examples of them include dl-α-tocopherol, d-δ-tocopherol and natural tocopherol.

The amount of the tocopherol compound used is at least 0.001 part by weight, preferably 0.001 to 0.01 part by weight, per part by weight of the polyprenyl compound of the above general formula (1). When the amount of the tocopherol is below this range, the effect is insufficient and, on the other hand, when it is above this range, an apparent discoloration is caused.

The organic acids used in the present invention include citric acid and tartaric acid. The amount or the organic acid used is 0.0005 to 0.004 part by weight, preferably 0.001 to 0.002 part by weight, per part by weight of the polyprenyl compound of the above general formula (1).

In the present invention, a mixture of the tocopherol compound with the organic acid may also be used. A particularly excellent stabilization effect can be obtained when the weight ratio of tocopherol to tartaric acid used is 1:1.

Thus, the present invention provides a process for producing a hard capsule formula (1), characterized in that a neutral or basic amino acid is incorporated thereinto.

The amino acids to be used in the present invention include neutral amino acids such as glycine, alanine, valine and leucine; and basic amino acids such as arginine. From the viewpoint of solubility and stability of the amino acids, glycine, alanine and valine are preferred.

The amount of neutral or basic amino acid used in the present invention is preferably 0.1 to 2.0% by weight based on the polyprenyl compound. Since impurities contained in the polyprenyl compound and decomposition products thereof might affect the insolubilization of the capsule shell, it is preferred to use 0.3% by weight or more of the neutral or basic amino acid in order to inhibit the insolubilization of the shell when 1.0% by weight or more of impurities or decomposition products are contained therein.

A hydrophilic colloid, antioxidant, lubricant, etc. usually used in the production of known hard capsules can be used in addition to the above-described indispensable components in the present invention.

The following Experimental Examples will further illustrate the effects of the present invention, In the Examples, the percentages are given by weight, unless otherwise stated.

EXPERIMENTAL EXAMPLE 1

Effect of Addition of Tocopherol 0.1 to 1.0% (0.014, 0.03, 0.06, 0.09, 0.12 or 0.15 g) of natural tocopherol was added to 15.0 g of Indometacin farnesyl to obtain a solution at 60° C. A mixture of 8.92 g of silicon dioxide hydrate with 0.5 g of methylcellulose was added to the solution and the mixture was kneaded. Then, a solution of 1 g of Macrogol 6000 and 0.08 g of glycine in water was added thereto and the mixture was kneaded, granulated and dried at 60° C. for 10 h.

After drying, the granules were sized to obtain granules having a diameter of 1000 μm. 1.1 g of Carplex, 0.25 g of Avicel, 0.1 g of Aerosil and 0.5 g of talc were added thereto as lubricants, etc. and the mixture was filled in a hard capsule.

The same procedure as that described above was repeated except that no natural tocopherol was used.

The hard capsules thus obtained were stored at 60° C. for one month and then the quantity of indomethacin farnesyl was determined to evaluate the stabilization effect of tocopherol.

Figure 1:
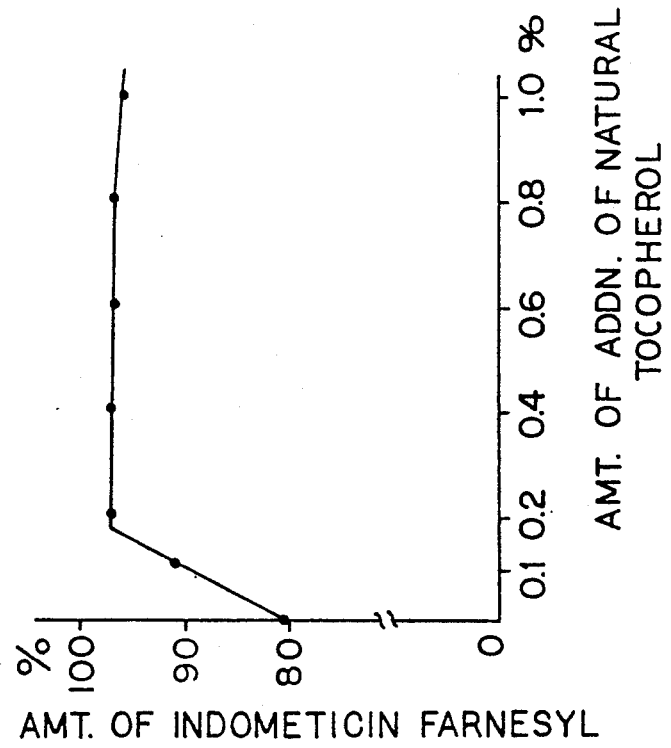

The results are given in FIG. 1.

It is apparent from the FIG. 1 that when 0.1% or more, based on indomethacin farnesyl, of natural tocopherol is added, the stabilization effect is obtained.

EXPERIMENTAL EXAMPLE 2

Stabilization Effect of Tartaric Acid 15 g of indomethacin farnesyl was melted at 60° C. A mixture of 8.92 g of silicon dioxide hydrate with 0.5 g of methylcellulose was added thereto and the mixture was kneaded. Separately, 1 g of Macrogol 6000, 0.80 g of glycine and 0.05 to 0.4%, based on indomethacin farnesyl, i.e., 0.008, 0.0015, 0.003, 0.0045 or 0.006 g of tartaric acid were dissolved in water and added to the above mixture, and the resulting mixture was kneaded, granulated and dried at 60° C. for 10 h.

After drying, the granules were sized to obtain granules having a diameter of 1000 μm. 1.1 g of Carplex, 0.25 g of Avicel, 0.1 g of Aerosil and 0.5 g of talc were added thereto and the mixture was filled in a hard capsule.

The same procedure as that described above was repeated except that no tartaric acid was used.

The hard capsules thus obtained were stored at 55° C. for one month and then the quality, based on indomethacin farnesyl, of a product formed by the elimination of the benzoyl group from indomethacin farnesyl was determined to evaluate the stabilization effect of tartaric acid.

Figure 2:
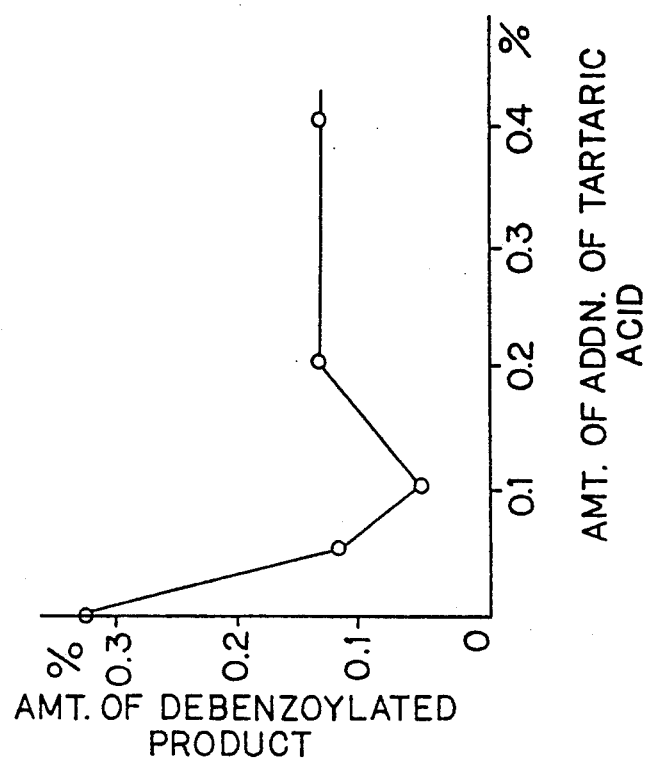
FIG. 1 is a graph showing the results obtained in Experimental Example 1 and FIG. 2 is a graph showing the results obtained in Experimental Example 2.

The results are given in FIG. 2.

It is apparent from the FIG. 2 that when 0.05%, based on indomethacin farnesyl, or more of tartaric acid was used, the elimination of the benzoyl group from the active ingredient was inhibited to exhibit a stabilization effect.

EXPERIMENTAL EXAMPLE 3

Synergistic Stabilization Effect of Tocopherol and Tartaric Acid

Natural tocopherol and tartaric acid in a weight ratio of 1:1, 1:2, 1:5 or 1:11 as specified in Table 1 were added to 15 g of indomethacin farnesyl and the mixture was melted at 60° C. A mixture of 8.92 g of silicon dioxide hydrate with 0.5 g of methylcellulose was added thereto and kneaded together.

A solution of 1 g of Macrogol 6000 and 0.08 g of glycine in water was added to the mixture and the resulting mixture was kneaded together, granulated and dried at 60° C. for 10 h.

After drying, the granules were sized to obtain granules having a diameter of 1000 μm. 1.1 g of Carplex, 0.25 g of Avicel, 0.1 g of Aerosil and 0.5 g of talc were added thereto and kneaded together.

The mixture was inserted into a hard capsule.

The hard capsules thus obtained were stored at 55° C. for 13 days and the quantities of the debenzoylated product and other decomposition products were determined to evaluate the synergistic stabilization effect of tocopherol and tartaric acid.

The results are given in Table 1.

TABLE 1

| Synergistic stabilization effect of tocopherol and tartaric acid | | | | |
|---|---|---|---|---|
| | Amount (%)[*1] | | | |
| Tocopherol | 0.03 | 0.16 | 0.03 | 0.16 |

TABLE 1-continued

| Synergistic stabilization effect of tocopherol and tartaric acid | | | | |
|---|---|---|---|---|
| Tartaric acid | 0.16 | 0.16 | 0.33 | 0.33 |
| | Amount of decomposition product (%)[*2] | | | |
| Debenzoylated compound | 0.06 | 0.07 | 0.05 | 0.02 |
| Other decomposition product | 1.85 | 1.66 | 3.08 | 2.55 |

Notes)
[*1]Weight % based on indomethacin farnesyl
[*2]Weight % based on the total products It is apparent from the Table 1 that a particularly excellent stabilization effect can be obtained when the ratio of tocopherol to tartaric acid is 1:1.

EXAMPLES

The following Examples will further illustrate the process of the present invention employed in producing hard capsules.

EXAMPLE 1

0.25 g of natural tocopherol was added to 150 g of indomethacin farnesyl and the mixture was heated to 60° C. to form a solution. A mixture of 89.2 g of silicon dioxide hydrate with 5.0 g of methylcellulose was added thereto and the mixtures were kneaded together.

A solution of 10 g of Macrogol 6000 and 0.8 g of glycine in water was added to the mixture and the resulting mixture was kneaded together, granulated and dried at 60° C. for 10 h.

After drying, the granules were sized to obtain granules having a diameter of 1000 μm. 11 g of Carplex, 2.5 g of Avicel, 1.0 g of Aerosil and 5.0 g of talc were added thereto and mixed therewith.

The mixture was filled in a hard capsule.

EXAMPLE 2

0.16 g of natural tocopherol was added to 100 g of indomethacin farnesyl to obtain a solution at 60° C. A mixture of 67.95 g of silicon dioxide hydrate with 3.3 g of methylcellulose was added thereto and the mixtures were kneaded together.

A solution of 6.6 g of Macrogol 6000 and 0.53 g of glycine in water was added to the mixture and the resulting mixture was kneaded together, granulated and dried at 60° C. for 10 h.

After drying, the granules were sized to obtain granules having a diameter of 1000 μm. 8 g of Carplex, 1.5 g of Avicel, 0.7 g of Aerosil and 3.5 g of talc were added thereto and mixed therewith.

The mixture was inserted into a hard capsule.

EXPERIMENTAL EXAMPLE 4

Study of Stabilization Effects of Different Types of Amino Acids

Method 67.8 mg of silicon dioxide hydrate (Siloid 244) was added to 5.0 mg of methylcellulose (Methocel 25) and mixed therewith. 86.7 mg of indomethacin farnesyl and 0.2 mg of dl-α-tocopherol, as an antioxidant, were added thereto to effect adsorption thereon.

1 mg of an amino acid was added to polyethylene glycol (PEG 6000) and then water was added thereto while heating to form a solution, which was added to the mixture obtained above. The obtained mixture was granulated and dried by an ordinary method. The granules were sized to obtain granules of a predetermined diameter. The sized granules inserted into a hard capsule to obtain a sample.

Aspartic acid and glutamic acid were used as the acidic amino acids and glycine and leucine were used as the neutral amino acids, while arginine was used as the basic amino acid.

The amino acid-containing capsule was kept in a vial at 55° C. for 5 days and 15 days to examine the dissolution on the capsule shell.

Results

The contents of the vial were taken out and the capsule was stirred in a first solution according to The Pharmacopoeia of Japan at 37° C. for 5 min to examine the extent of dissolution of the capsule.

The results are given in Table 2.

TABLE 2

| | No amino acid | Acidic amino acid | | Neutral amino acid | | Basic amino acid |
|---|---|---|---|---|---|---|
| | | aspartic acid | glutamine | glycine | leucine | arginine |
| 5 days | ++ | + | + | − | − | − |
| 15 days | ++ | + | + | − | − | − |

Notes)
The extent of the dissolution was evaluated on the basis of the following criteria:
++: The shell did not dissolve (remained in film form)
+: The shell did not dissolve (remained in filament form)
−: The shell dissolved.

It is apparent from Table 2 that neither the neutral nor the basic amino acid insolubilizes the capsules.

EXPERIMENTAL EXAMPLE 5

Study on the Effect on the Amount of Glycine

Method 67.8 mg of silicon dioxide hydrate was added to 5.0 mg of methylcellulose and thoroughly mixed therewith. 86.7 mg of indomethacin farnesyl containing 0.07, 0.36, 1.06 or 2.05% of impurities was added thereto and then 0.2 mg of dl-tocopherol, as an antioxidant, was added thereto to effect adsorption thereon.

0.1, 0.3, 1.0 or 2.0 mg/C of glycine was added to polyethylene glycol and then water was added thereto, while heating, to obtain a solution which was added to the mixture obtained above. The obtained mixture was granulated and the granules were dried by an ordinary method. The granules were sized to obtain granules having a predetermined diameter and inserted into a hard capsule to obtain a sample.

The hard capsule containing impurities and glycine was kept at 55° C. or 40° C. and a relative humidity of 75% for one month to examine the dissolution of the capsule shell.

Results

The results are given in Table 3.

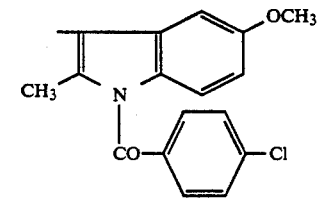
(1)

TABLE 3

Solubility of capsule shell after storage at 55° C. or 40° C. at RH of 75% for 1 month

| ill-treatment Impurity content | Glycine 0 mg/c 55° C. | 0 mg/c 40° C. × RH 75% | 0.1 55°C. | 0.1 40° C. × RH 75% | 0.3 55°C. | 0.3 40° C. × RH 75% | 1.0 55°C. | 1.0 40° C. × RH 75% | 2.0 55°C. | 2.0 40° C. × RH 75% |
|---|---|---|---|---|---|---|---|---|---|---|
| 0.07% | + | ++ | − | − | − | − | − | − | − | − |
| 0.36 | + | ++ | − | − | − | − | − | − | − | − |
| 1.06 | + | ++ | − | + | − | − | − | − | − | − |
| 2.05 | ++ | ++ | + | ++ | − | + | − | − | − | − |

Note) The criteria for the solubility were the same as those of Table 1.

It is apparent from the Table 3 that when the impurity content of indomethacin farnesyl is 1.0% or less, the insolubilization of the capsule shell can be inhibited with 0.3 mg/C of glycine.

EXAMPLES

The following Example will further illustrate the present invention but by no means limits the invention.

EXAMPLE 3

0.32 g of natural tocopherol was added to 200 g of indomethacin farnesyl to obtain a solution at 60° C. A mixture of 135.9 g of silicon dioxide hydrate with 6.6 g of methylcellulose was added to the solution and kneaded therewith.

A solution of 13.2 g of Macrogol 6000, 1.06 g of glycine and 0.32 g of tartaric acid in water was added to the mixture, kneaded therewith and granulated, and the obtained granules were dried at 60° C. for 10 h.

After the completion of the drying, the granules were sized to obtain granules having a granule diameter of 1000 μm, and 1.5 g of Carplex, 3.0 g of Avicel, 1.5 g of Aerosil and 0.6 g of talc were added thereto.

The obtained mixture was inserted into a hard capsule.

We claim:

1. A method for stabilizing a polyprenyl compound of formula (1), comprising the step of mixing said compound with one or more stabilizing agents selected from the group consisting of 0.001 to 0.01 part by weight dl-α-tocopherol and 0.0005 to 0.004 part by weight of an organic acid selected from the group consisting of citric acid and tartaric acid:

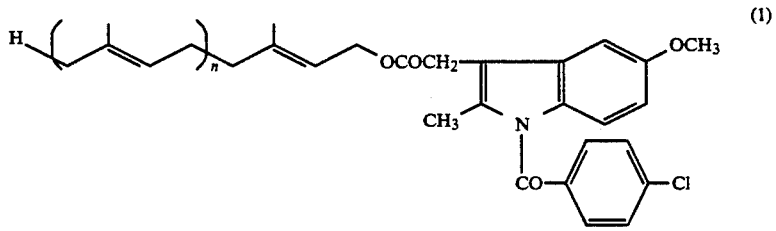
(1)

in which n is an integer of 1 to 3 and said part by weight is based on the weight of the polyprenyl compound.

2. The method as claimed in claim 1, in which the polyprenyl compound is 3,7,11,15-tetramethyl-2,6,10,14-hexadecatetraenyl 1-(p-chlorobenzoyl)-2-methyl-5-methoxy-3-indolylacetate or indomethacin farnesyl.

3. The method as claimed in claim 1, in which the stabilizing agent is dl-α-tocopherol.

4. The method as claimed in claim 1, in which the stabilizing agent is selected from the group consisting of citric acid and tartaric acid.

5. A stabilized composition produced by the method as defined in claim 1.

6. A method for stabilizing a gelatin-containing capsule shell containing a polyprenyl compound of formula (1) comprising the step of mixing said compound with 0.1 to 2.0% by weight of a neutral or basic amino acid:

in which n is an integer of 1 to 3, said percent by weight being based on the weight of the polyprenyl compound.

7. A composition comprising a gelatin-containing capsule shell, a polyprenyl compound of formula (1) encapsulated within said shell and 0.1 to 2.0% by weight of a neutral or basic amino acid mixed with said polyprenyl compound:

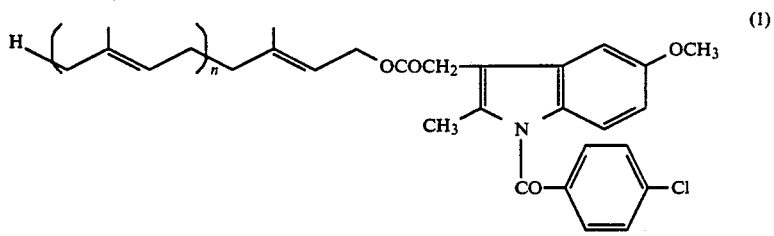

in which n is an integer of 1 to 3, said percent by weight being based on the weight of the polyprenyl compound.

8. A pharmacological composition comprising a therapeutically effective amount of a polyprenyl compound of formula (1) for treating an inflammation and an effective amount of a stabilizing agent selected from the group consisting of 0.001 to 0.01 part by weight of dl-α-tocopherol and 0.0005 to 0.004 part by weight of an organic acid selected from the group consisting of citric acid and tartaric acid for stabilization of said polyprenyl compound:

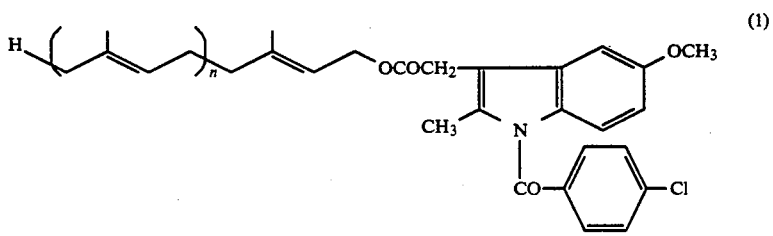

in which n is an integer of 1 to 3 and said part by weight is based on the weight of the polyprenyl compound.

9. The composition as claimed in claim 8, additionally comprising a pharmacologically acceptable carrier.

10. The composition as claimed in claim 8, in which the stabilizing agent is dl-α-tocopherol.

11. The composition as claimed in claim 8, in which the stabilizing agent is selected from the group consisting of citric acid and tartaric acid.

* * * * *